(12) United States Patent
Kiev

(10) Patent No.: US 9,743,953 B2
(45) Date of Patent: Aug. 29, 2017

(54) DEVICE AND METHOD FOR ACCESS TO INTERIOR BODY REGIONS

(71) Applicant: Jon Kiev, Vernon Hills, IL (US)

(72) Inventor: Jon Kiev, Vernon Hills, IL (US)

(73) Assignee: Jon Kiev, Lexington, KY (US)

( * ) Notice: Subject to any disclaimer, the term of this patent is extended or adjusted under 35 U.S.C. 154(b) by 71 days.

(21) Appl. No.: 14/825,203

(22) Filed: Aug. 13, 2015

(65) Prior Publication Data

US 2016/0235437 A1    Aug. 18, 2016

Related U.S. Application Data

(63) Continuation-in-part of application No. 14/624,818, filed on Feb. 18, 2015.

(51) Int. Cl.
*A61M 5/178* (2006.01)
*A61B 17/34* (2006.01)
*A61B 17/3209* (2006.01)
*A61B 17/00* (2006.01)

(52) U.S. Cl.
CPC .... *A61B 17/3415* (2013.01); *A61B 17/32093* (2013.01); *A61B 17/3474* (2013.01); *A61B 17/3496* (2013.01); *A61B 2017/00809* (2013.01); *A61B 2017/346* (2013.01)

(58) Field of Classification Search
CPC .......... A61M 17/3403; A61M 14/3417; A61M 25/01; A61M 25/09; A61M 29/02; A61M 39/06; A61M 25/0625; A61M 2005/325; A61M 2025/0008; A61M 2039/244; A61M 25/0043; A61M 25/007; A61M 25/0102; A61M 25/06; A61M 17/34; A61M 25/0668; A61M 25/0693; A61M 25/0618; A61M 25/0662; A61M 25/09041; A61M 2025/0687; A61M 2025/09125; A61M 25/0105; A61M 25/0631; A61M 25/0637; A61M 25/0643; A61M 5/3257
See application file for complete search history.

(56) References Cited

U.S. PATENT DOCUMENTS

| | | | |
|---|---|---|---|
| 4,535,773 | A | 8/1985 | Yoon |
| 5,066,288 | A | 11/1991 | Deniega et al. |
| 5,152,754 | A | 10/1992 | Plyley et al. |
| 5,295,977 | A | 3/1994 | Cohen et al. |
| 5,314,417 | A | 5/1994 | Stephens et al. |

(Continued)

FOREIGN PATENT DOCUMENTS

EP          0135364       3/1985
GB     WO 2014006403 A1 *  1/2014   ........ A61M 25/0026

*Primary Examiner* — Bhisma Mehta
*Assistant Examiner* — Nawal Boufrou
(74) *Attorney, Agent, or Firm* — Evan D. Linderman

(57) ABSTRACT

A device and method is provided to gain access to interior body regions. The system includes a stylet needle assembly, a safety needle assembly, a blade assembly, a retractable obturator assembly, and a dilator assembly. The safety needle assembly accesses an interior body region, after which the blade assembly expands the pathway created by the safety needle assembly. The obturator then further expands the pathway and delivers the dilator assembly to the desired location. The safety needle assembly, obturator assembly, and blade assembly are removed, leaving the dilator assembly in place for future procedures.

7 Claims, 11 Drawing Sheets

(56) References Cited

U.S. PATENT DOCUMENTS

| | | | |
|---|---|---|---|
| 5,342,382 A | 8/1994 | Brinkerhoff et al. | |
| 5,387,197 A | 2/1995 | Smith et al. | |
| 5,624,459 A | 4/1997 | Kortenbach et al. | |
| 5,674,237 A | 10/1997 | Ott | |
| 5,779,680 A | 7/1998 | Yoon | |
| 5,855,566 A | 1/1999 | Dunlap et al. | |
| 5,984,941 A | 11/1999 | Wilson et al. | |
| 6,017,356 A * | 1/2000 | Frederick | A61B 17/3417 604/264 |
| 6,056,766 A * | 5/2000 | Thompson | A61B 17/3421 606/108 |
| 6,063,099 A | 5/2000 | Danks et al. | |
| 6,447,527 B1 | 9/2002 | Thompson et al. | |
| 7,367,960 B2 | 5/2008 | Stellon et al. | |
| 7,731,730 B2 | 6/2010 | Popov | |
| 8,940,007 B2 | 1/2015 | Smith et al. | |

\* cited by examiner

DEVICE AND METHOD FOR ACCESS TO INTERIOR BODY REGIONS

CROSS-REFERENCE TO RELATED APPLICATIONS

Pursuant to 35 U.S.C. §120, this application is a continuation-in-part of, and claims priority to, co-pending U.S. patent application Ser. No. 14/624,818, filed Feb. 18, 2015, which is incorporated by reference herein in its entirety.

TECHNICAL FIELD

The present invention relates to devices and methods to access interior body regions. More particularly, it relates to devices and methods used to create space to insert a tube into a patient.

BACKGROUND

Embodiments of the invention relate to devices to create access to interior body regions and methods of using the devices.

There are many instances in which a practitioner must access the chest, abdomen, or pelvis, and insert a drainage tube, or chest tube. Examples of these instances include: collapsed lung, lung infection, bleeding in the chest cavity, fluid or air buildup due to other medical conditions or trauma, and prior surgery.

The traditional way of inserting a chest tube begins with the practitioner prepping the side of the body for the chest tube by sterilizing the area. Using a scalpel, the practitioner then makes a small incision (skin nick), between the ribs closest to the desired location in the chest. Then, using a combination of blunt dissection and surgical clamps, the practitioner will slowly open the space and extend it into the chest cavity. Once the practitioner confirms she has reached the desired space, the chest tube is inserted and sutured in place to prevent slippage.

Critics claim that the traditional method of chest tube insertion is barbaric and does not take advantage of advances in technology that can make the insertion process safer and more effective. Some companies have designed devices, called trocars, to facilitate safer and easier chest tube placement without using multiple, separate components.

Many groups of trocars include a combination of a safety needle, an obturator and a dilator. The doctor advances the device against the skin and interior body regions using the safety needle. As the doctor advances the device through the body, the obturator expands the pathway created by the safety needle. When the device reaches the desired area, the practitioner removes the safety needle and the obturator from the dilator, leaving the dilator in place. The practitioner then pushes the chest tube through the dilator and removes the dilator, leaving the chest tube in the desired location.

Problems arise with these types of trocars, however, because the obturator does not actually work very well in expanding the pathway created by the relatively small safety needle. The skin provides a tough membrane that resists expansion, and additional skin nicks (using a separate scalpel) are required around the safety needle to allow the obturator to properly expand the skin layer and continue to penetrate deeper into the body.

To address this issue, other groups of trocars employ a retractable blade instead of a safety needle. The blade is used to create a larger skin nick and advance through other tissues as needed until reaching the desired location. The obturator easily expands the pathway as it passes through the skin layer while the practitioner advances the device, and then the blade is retracted and the blade/obturator combination is removed, leaving the dilator in place for the chest tube.

While these groups of trocars address the issue of requiring an additional scalpel to allow the obturator to expand the skin layer, they do not include the safety needle that prevents the doctor from progressing too quickly or too far and causing harm to the patient. Without the safety needle as part of the system, the patient is at a greater risk of complications.

Other groups of trocars include a fixed blade with an obturator with a retractable shield that can expose the blade when the user presses the shield against the skin. The blade creates a larger skin nick, and when the blade reaches an area of lower resistance, the shield automatically advances, covering the blade. Presuming that the area of lower resistance is the desired location, the user removes the blade/obturator combination, leaving the dilator in place for the chest tube.

While these groups of trocars address the issue of providing a safe way to advance the blade into the desired location, they do not provide a way for a user to verify the trocar is in the correct location by aspirating a fluid sample prior to inserting a chest tube. Without confirming the location of the device before chest tube placement, the patient is at greater risk of complications.

What is needed in the market is an all-in-one trocar device that provides the ability to create a skin nick, maintain safety, and aspirate fluid as the device is inserted deeper into the body, while quickly accessing the desired location for chest tube placement.

BRIEF SUMMARY OF THE INVENTION

Benefits achieved in accordance with principles of the disclosed invention include a device that provides access to interior body regions.

Some aspects of the present invention relate to a safety needle assembly, a blade assembly, an obturator assembly, and a dilator assembly. The safety needle assembly, blade assembly, obturator assembly, and dilator assembly are assembled to create an access device.

In some aspects of the present invention, the blade assembly includes multiple blades, while in other aspects of the present invention, the blade assembly includes a single blade.

In other aspects of the present invention, the safety needle assembly includes a hub through which fluid may be drawn in order to confirm the device has reached the proper location within the body.

In further aspects of the present invention, the blade assembly and safety needle assembly are longitudinally coaxial, while in still further aspects of the present invention, the blade assembly and safety needle assembly are not longitudinally coaxial.

Yet other aspects of the present invention relate to a method of accessing interior body regions in which the safety needle assembly is advanced through skin and into interior body regions to create a pathway. The blades of the blade assembly are deployed and the blade assembly is advanced into the skin to create a skin nick, after which the blades are retracted. The access device is then advanced into the tissue, and the obturator assembly increases the diameter of the pathway created by the safety needle. After the access device is in the proper location, the safety needle assembly, blade assembly, and obturator assembly are removed from the dilator assembly, leaving the dilator assembly in the body to provide a conduit through which other devices may be inserted.

Other aspects of the present invention relate to a stylet assembly, a blade assembly, an obturator assembly, and a dilator assembly. The stylet assembly, blade assembly, obturator assembly, and dilator assembly are assembled to create an access device.

In some aspects of the present invention, the blade assembly include a lumen through which the stylet assembly is received.

In yet other aspects of the present invention, a safety needle assembly may be received through the lumen of the blade assembly. The safety needle assembly may provide the ability to withdraw fluid from a location within the body.

In some aspects of the present invention, the obturator assembly includes a retractable shield that covers the blade assembly when the access device is not being inserted into the skin, and reveals the blade assembly when the access device is being inserted into the skin.

BRIEF SUMMARY OF THE DRAWINGS

The accompanying drawings, which are incorporated in and form a part of the specification, illustrate example embodiments and, together with the description, serve to explain the principles of the invention. In the drawings.

DETAILED DESCRIPTION

Figure 1:
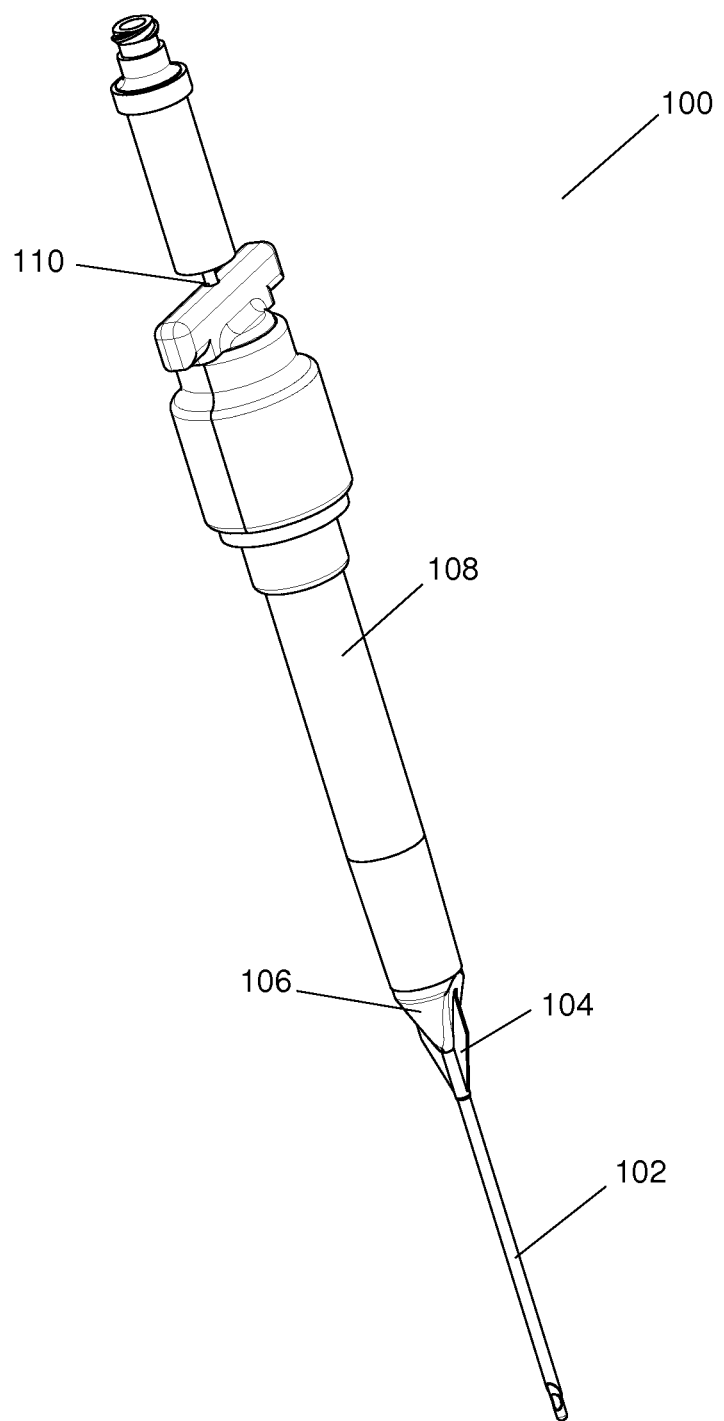
FIG. 1 illustrates an insertion device according to aspects of the present invention.

FIG. 1 illustrates an insertion device according to aspects of the present invention.

As shown in the figure, insertion device 100 includes safety needle 102, blade assembly 104, obturator assembly 106, dilator assembly 108, and handle hole 110.

Specific aspects of safety needle 102, blade assembly 104, obturator assembly 106, and dilator assembly 108 will be further described with reference to FIGS. 2, 3, 4, and 8, respectively.

In general, insertion device 100 is assembled by inserting safety needle assembly 102 through handle hole 110 and into blade assembly 104 until safety needle assembly 102 is distal to the distal end of blade assembly 104. Then, the combination of safety needle assembly 102 and blade assembly 104 is inserted through obturator assembly 106. Then, obturator assembly 106, blade assembly 104, and safety needle assembly 102 are connected to dilator assembly 108. A more detailed description of the assembly and operation of insertion device 100 will be further described with reference to FIGS. 2-8.

Figure 2:
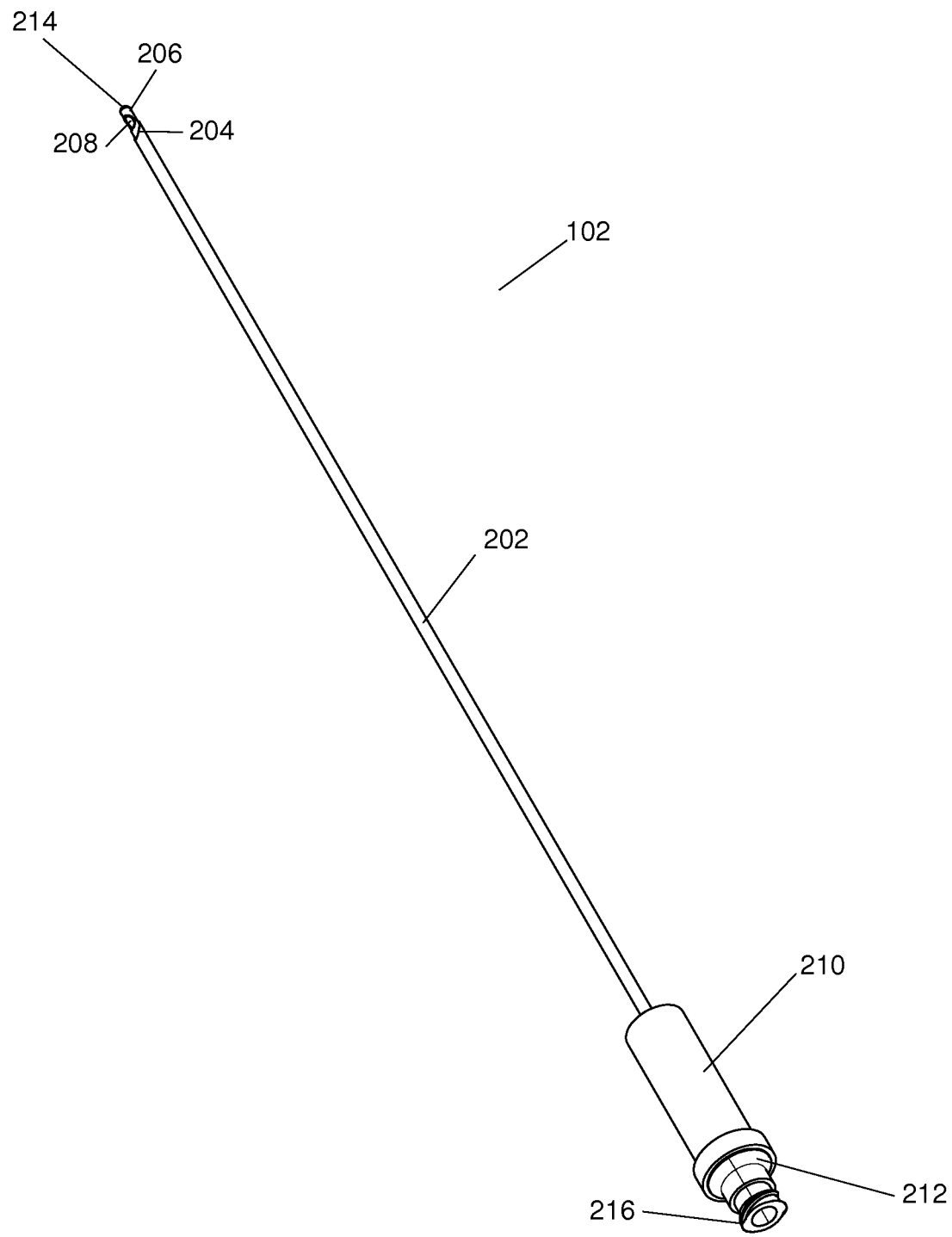
FIG. 2 illustrates a safety needle according to aspects of the present invention.

FIG. 2 illustrates a safety needle according to aspects of the present invention.

As shown in the figure, safety needle 102 includes cannula 202, cannula tip 204, stylet 206, stylet port 208, stylet tip 214, housing 210, hub 212, and connection means 216.

Cannula 202 is preferably constructed from a generally rigid material, such as metal or plastic, but other rigid materials may be considered. It may be extruded, welded, molded, or manufactured by any other method that would result in a generally rigid material. Cannula 202 is connected to hub 210 such that there is no relative movement between hub 210 and cannula 202. The connection may be via any mechanical means (a non-limiting example of which includes overmolding), adhesive means (a non-limiting example of which includes UV adhesive), or any other means that would create a bond between housing 210 and cannula 202 to prevent relative motion between the two components.

Cannula tip 204 is designed to penetrate through tissue, and therefore it is relatively sharp. Cannula tip 204 may be manufactured by any known means to create a beveled tip, a conical tip, a crown tip, or any other geometry that is known in the art to provide a tip sharp enough to penetrate tissue.

Stylet 206 is preferably constructed from a generally rigid material, such as metal or plastic, but other rigid materials may be considered. It may be extruded, welded, molded, or manufactured by any other method that would result in a generally rigid material. Stylet 206 is connected to housing 210 such that there may be relative motion between the two components. The outer diameter of stylet 206 is smaller than the inner diameter of cannula 202, and stylet 206 is slidably positioned inside of cannula 202.

Figure 6:
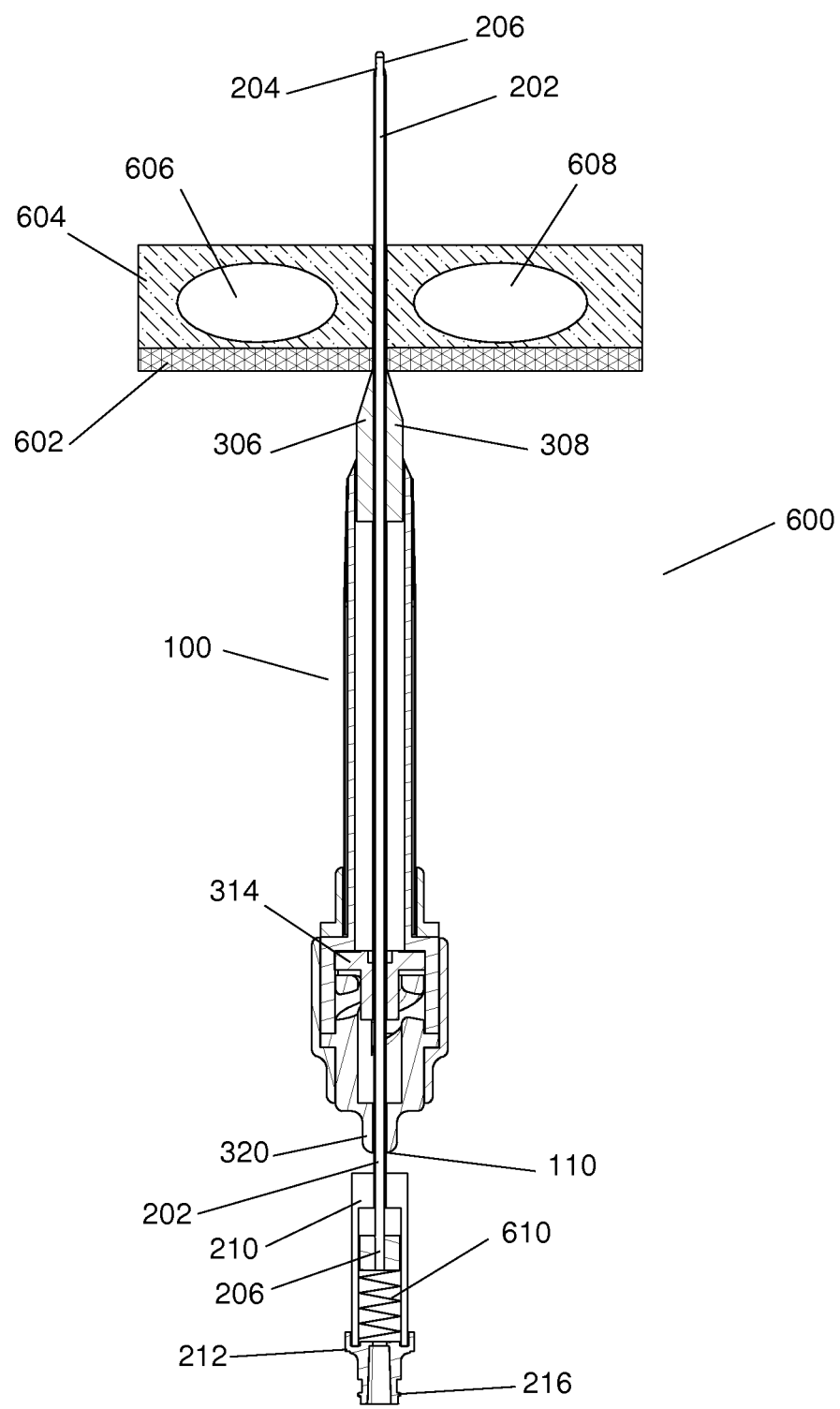
FIG. 6 illustrates a first step in inserting the insertion device according to aspects of the present invention.

Referring now to FIG. 6, housing 210 is a generally rigid component that is either machined or molded out of plastic. Housing 210 is connected to cannula 202 and to hub 212. The center of housing 210 is open to accommodate spring 610 and allow spring 610 to be compressed and uncompressed during use.

Stylet 206 is connected to spring 610 via any mechanical, chemical or adhesive means that would create a bond between the two components. In an alternate embodiment, stylet 206 and spring 610 may both be connected to an intermediate part, such that stylet 206 and spring 610 are effectively bonded together. Spring 610 is connected to housing 210 and hub 212 via any mechanical, chemical or adhesive means that would create bond between the two components. In yet another alternate embodiment, spring 610 may freely float in between stylet 206 and hub 212 such that no bond between components is required.

Referring back to FIG. 2, stylet tip 214 is designed to avoid penetrating through tissue, and therefore it is relatively blunt and closed at the distal end. Stylet tip 214 may be manufactured by any known means to create a curved tip, a bullet tip, a flat tip, or any other geometry that is known in the art to create a closed distal tip that will avoid penetrating tissue.

Stylet port 208 is an open section in stylet 206 that is proximal to stylet tip 214 and distal to cannula tip 204 when spring 610 is uncompressed. Stylet port 208 may be manufactured by traditional grinding or machining techniques or by more advanced techniques, including electric discharge machining (EDM), chemical etching, or laser machining.

Referring back to FIG. 6, hub 212 is a generally rigid component that is either machined or molded out of plastic. Hub 212 is connected to spring 610 and to housing 210. Hub 212 includes connection means 216 such that hub 212 may be connected to an external source for fluid drainage or administration.

Referring back to FIG. 2, connection means 216 is shown as a threaded connection, however any suitable connection means (a non-limiting example of which includes a snap fit) that provide for connection of a fluid drainage or administration device is acceptable.

Referring to FIGS. 2 and 6, in operation, a user grasps hub 210 or another component that may be coupled to hub 210 and advances safety needle assembly 102 toward a patient's skin. The first component of safety needle assembly 102 that contacts the skin is stylet tip 214. As the user continues to push safety needle assembly 102 into the skin, the blunt stylet tip 214 transfers the pushing force through stylet 206, compresses spring 610, causes cannula 202 to move relative to stylet 206, and allows cannula tip 204 to move toward the skin.

When the pushing force is sufficient enough, cannula tip 204 will contact the skin and the sharp tip will penetrate the skin and soft tissues underneath the skin. When cannula tip 204 reaches an area of little or no resistance, spring 610 will uncompress, allowing stylet 206 to move forward again such that stylet tip 214 is distal to cannula tip 204, and stylet port 208 is exposed to the area. Areas of little or no resistance include fluid (or air) filled spaces such as the plerua, lungs, or any other fluid filled space the user desires to reach.

To confirm that safety needle assembly 102 is in the correct location, the user may connect a fluid drainage device to connection means 216 and use the fluid drainage device to pull fluid or air from the area as means of confirmation. Fluid drainage devices that may be used include syringes, suction canisters, wall suction, and any other means that may operate to pull fluid from the patient to confirm appropriate placement of safety needle assembly 102.

Figure 3:
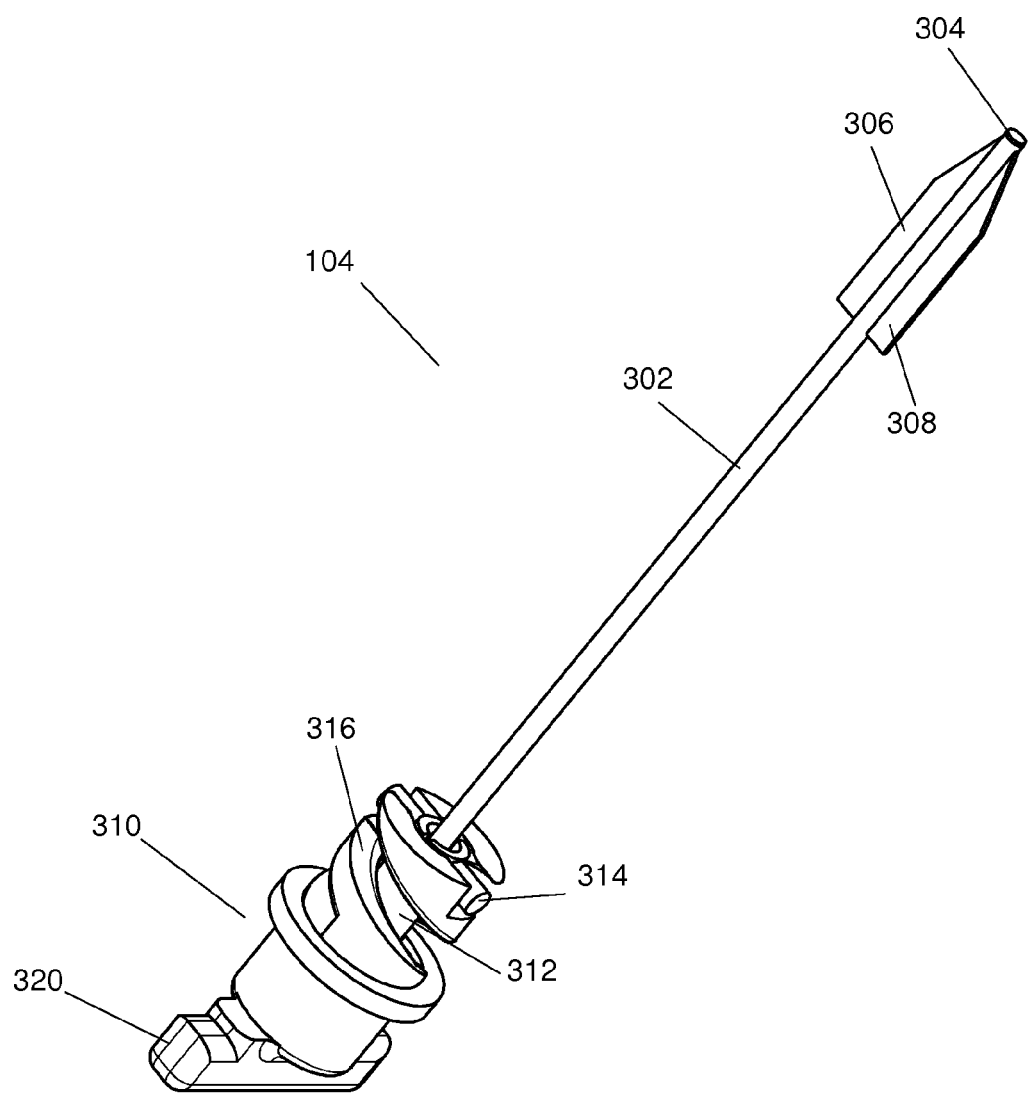
FIG. 3 illustrates a blade assembly according to aspects of the present invention.

FIG. 3 illustrates a blade assembly according to aspects of the present invention.

As shown in the figure, blade assembly 104 includes shaft 302, distal tip 304, blades 306 and 308, handle 310, follower shaft 312, and follower 314.

Shaft 302 is a rigid tube and is preferably made of metal, however any other rigid material would suffice. Shaft 302 is connected to follower shaft 314 such that there is no relative motion between the two components. The connection may be made via mechanical, adhesive, or chemical means. Shaft 302 is also connected to blades 306 and 308. The connection is preferably a welded connection, however other connection means may be employed. For example, shaft 302 may contain one or more slots at its distal end and blades 306 and 308 may contain one or more matching slots such that blades 306 and 308 may be assembled on to shaft 302 by sliding slotted sections of blades 306 and 308 on to the corresponding slots at the distal end of shaft 302.

Distal tip 304 is at the distal end of shaft 302 and is operable to provide a leading edge for blades 306 and 308. Distal tip 304 may be produced by any conventional tip grinding or finishing process, and it may be a beveled tip, a conical tip, a crown tip, or any other tip that would provide an appropriate leading edge for blades 306 and 308.

Blades 306 and 308 are preferably constructed from metal, more preferably from stainless steel, however any material suitable for medical applications would suffice. Blades 306 and 308 are operable to cut the skin of a patient, and as such are sufficiently sharp to cut skin. The specific shape, grind angles, and tip angles may be of any dimensions such that the effect of cutting skin may be accomplished. Blades 306 and 308 are attached to shaft 302 as previously described.

Handle 310 includes handle top 320 and cam 316. Handle 310 is preferably made of plastic via either machining or molding, however any other suitable materials or manufacturing methods may be used. Handle top 320 is designed to be gripped by a user in order to rotate handle 310 relative to follower shaft 312 and follower 314. Rotating handle top 320 and the motion of follower shaft 312 and follower 314 will be further discussed with reference to operation of blade assembly 104 below. Cam 316 is a slot within handle 310 in which follower 314 travels. Cam 316 may be constructed with any geometry that will provide the desired motion of follower 314.

Follower 314 and follower shaft 312 are both preferably made of plastic via either machining or molding, however any other suitable materials or manufacturing methods may be used. In some embodiments, follower 314 and follower shaft 312 may be a single component, however they are shown here as two separate components. Follower 314 and follower shaft 312 are bonded together by any suitable means that will effectively prevent relative motion between the two components. In addition, shaft 302 is bonded to follower 314 and follower shaft 312 to prevent relative motion between the three components.

In operation, a user will turn handle 310 to effect a linear movement of shaft 302. The user will grasp handle top 320 with one hand and dilator assembly 108 (not shown) with the other hand. Handle 310 therefore only rotates, and does not move in a linear direction when handle top 320 is turned. FIG. 3 shows blade assembly 104 with blades 306 and 308 fully deployed. To retract blades 306 and 308, the user would turn handle top 320 in the appropriate direction. Turning handle top 320 causes cam 316 to rotate. As cam 316 rotates, follower 314 moves in a linear manner such that follower 314 moves closer to handle top 320. To deploy blades 306 and 308, the user would turn handle top 320 in the opposite direction.

Figure 4:
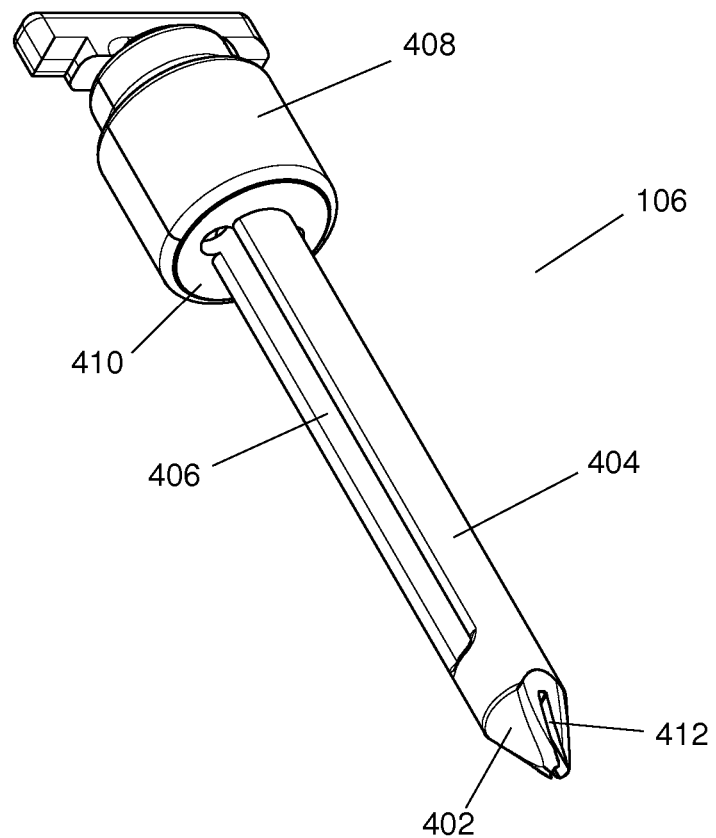
FIG. 4 illustrates an obturator assembly according to aspects of the present invention.

FIG. 4 illustrates an obturator assembly according to aspects of the present invention.

As shown in the figure, obturator assembly 106 includes obturator tip 402, obturator shaft 404, handle cover 408, and obturator hub 410. All components of obturator assembly 106 are preferably made from plastic via either machining or molding processes, however any suitable material or manufacturing method may be used to create the component.

Obturator tip 402 is operable to enlarge an opening in the skin, and includes blade slot 412. Blade slot 412 is operable to provide a pathway for blades 306 and 308 to be deployed beyond the distal-most portion of obturator tip 402 and to be fully retracted within obturator tip 402. Obturator tip 402 is connected to obturator shaft 404 by any suitable means that would prevent relative motion between the two components. In an alternate embodiment, obturator tip 402 and obturator shaft 404 may be a single component.

Obturator shaft 404 is operable to travel within the enlarged opening created by obturator tip 402, and includes obturator slot 406. Obturator slot 406 is present to reduce weight and manufacturing costs. In an alternate embodiment, obturator slot 406 may be omitted entirely such that obturator shaft 404 is a continuous tube with no openings in its diameter.

Obturator hub 410 is connected to obturator shaft 404 by any means that would create a bond to prevent relative motion between the two components. Obturator hub 410 is operable to constrain the linear motion of follower 314 (not shown), such that blades 306 and 308 can only extend from obturator tip 402 by a defined distance.

Handle cover 408 is operable to attach to obturator hub 410 and cover cam 316 (not shown) such that a user cannot interfere with the operation of cam 316. Handle cover 408 may be a single component or multiple components that can be attached together. Additionally, in an alternate embodiment, handle cover 408 and obturator hub 410 may be a single component.

Returning to FIG. 1, and with reference to FIGS. 2-4, assembly of insertion device 100 will be described.

To assemble insertion device 100, safety needle 102 is inserted through handle hole 110 and extends through the inner diameter of shaft 302 of blade assembly 104, extending beyond distal tip 304. The combination of safety needle 102 and blade assembly 104 is inserted through the inner diameter of obturator shaft 404 until obturator hub 410 contacts cam 316 of blade assembly 104. Handle cover 408 is then installed to cover cam 316. Finally, the entire assembly is inserted through the inner diameter of dilator assembly 108 to complete the assembly process. There are no connections between dilator assembly 108 and the rest of the components; a simple press-fit interaction serves to keep dilator assembly 108 connected to the rest of the components. In an alternate embodiment, dilator assembly 108 may detachably lock to obturator assembly 106. Dilator assembly 108 will be further described with reference to FIGS. 6-8.

Figures 5A, 5B:
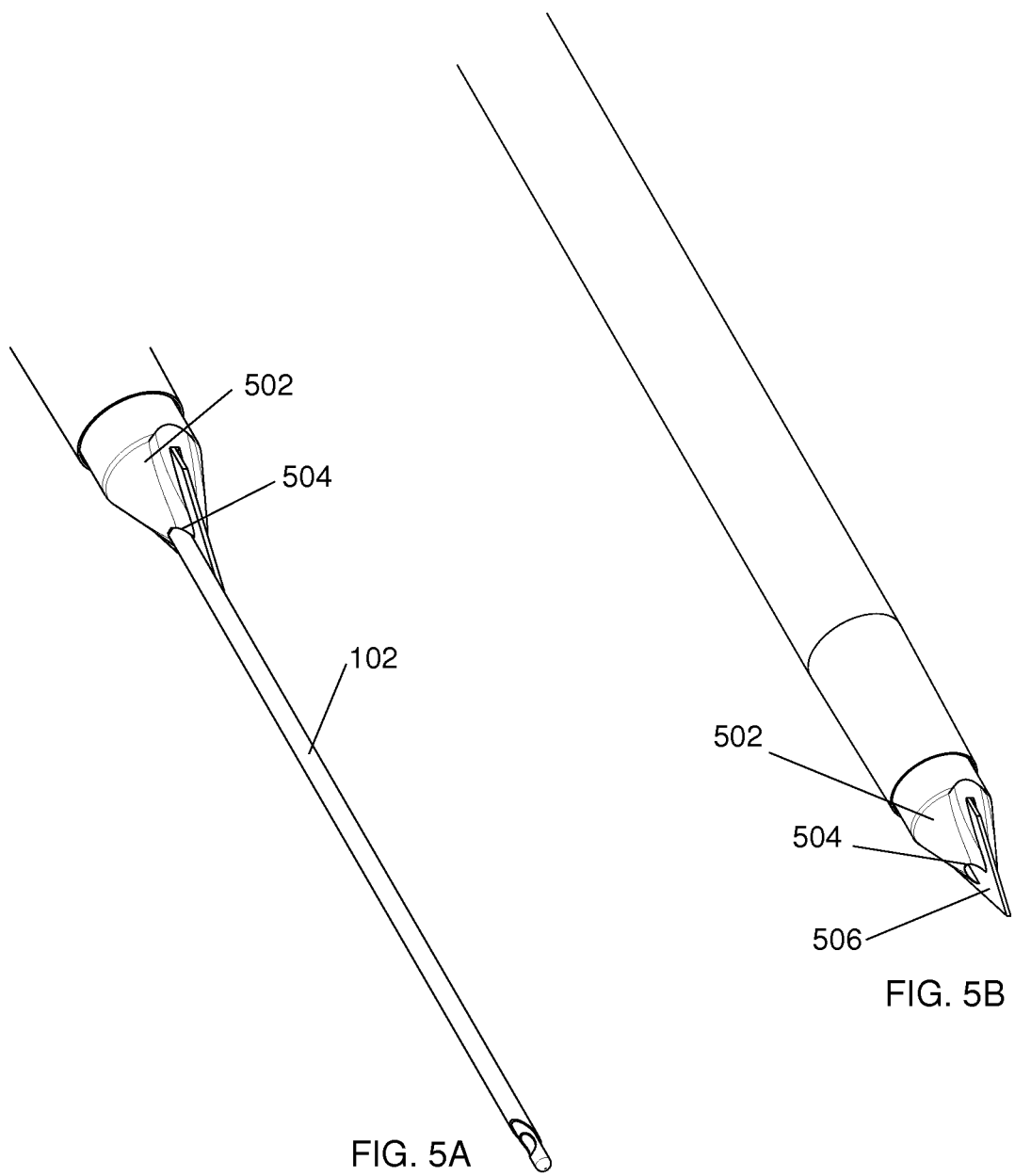
FIGS. 5A-B illustrate an alternate embodiment of a blade assembly and an obturator assembly according to aspects of the present invention.

FIGS. 5A-B illustrate an alternate embodiment of a blade assembly and an obturator assembly according to aspects of the present invention.

As shown in the figures, obturator tip 502 includes cutout 504 to accommodate safety needle 102. A blade slot similar to blade slot 412 provides space for blade 506 to deploy and retract.

In this embodiment, blade 506 is a single blade instead of multiple blades as previously described. The single blade may be attached to shaft 302 by any means previously described. If attaching multiple blades to the outer diameter of shaft 302 is difficult to accomplish, this alternate embodiment may be employed, as methods to attach a single blade to a shaft are well known in the art.

In attaching blade 506 to shaft 302, a difficulty is encountered as safety needle 102 and blade 506 cannot be longitudinally coaxial with each other as is possible with the multiple blade design. Therefore, it is necessary to create cutout 504 to accommodate safety needle assembly 102. In this embodiment, blade 506 slides along the outer diameter of safety needle assembly 102.

Testing has proven that, even though safety needle 102 is not concentric with respect to the rest of insertion device 100, the ability of blade 506 to enlarge the pathway created by safety needle 102 is not impacted, and the performance of insertion device 100 is not diminished.

In yet another alternate embodiment, and with further reference to FIGS. 3-4, it may be desirable to eliminate the need to turn handle 320 to deploy and retract blades 306 and 308. In such an embodiment, blade assembly 104 may contact a spring that rests on obturator hub 410. There may be a window in handle cover 408 such that the user's finger could reach blade assembly 104 through the window. Access to blade assembly 104 may also be available via obturator slot 406. When the user desires to deploy the blades, the user would extend a finger into the window and press down on blade assembly 104, compressing the spring and exposing the blades. After using the blades, the user would remove his/her finger from blade assembly 104, which would then automatically retract blades 306 and 308 into obturator assembly 106 as the spring uncompressed.

FIG. 6 illustrates a first step in inserting the insertion device according to aspects of the present invention.

As shown in the figure, system 600 includes skin 602, soft tissue 604, and ribs 606 and 608.

Figure 7:
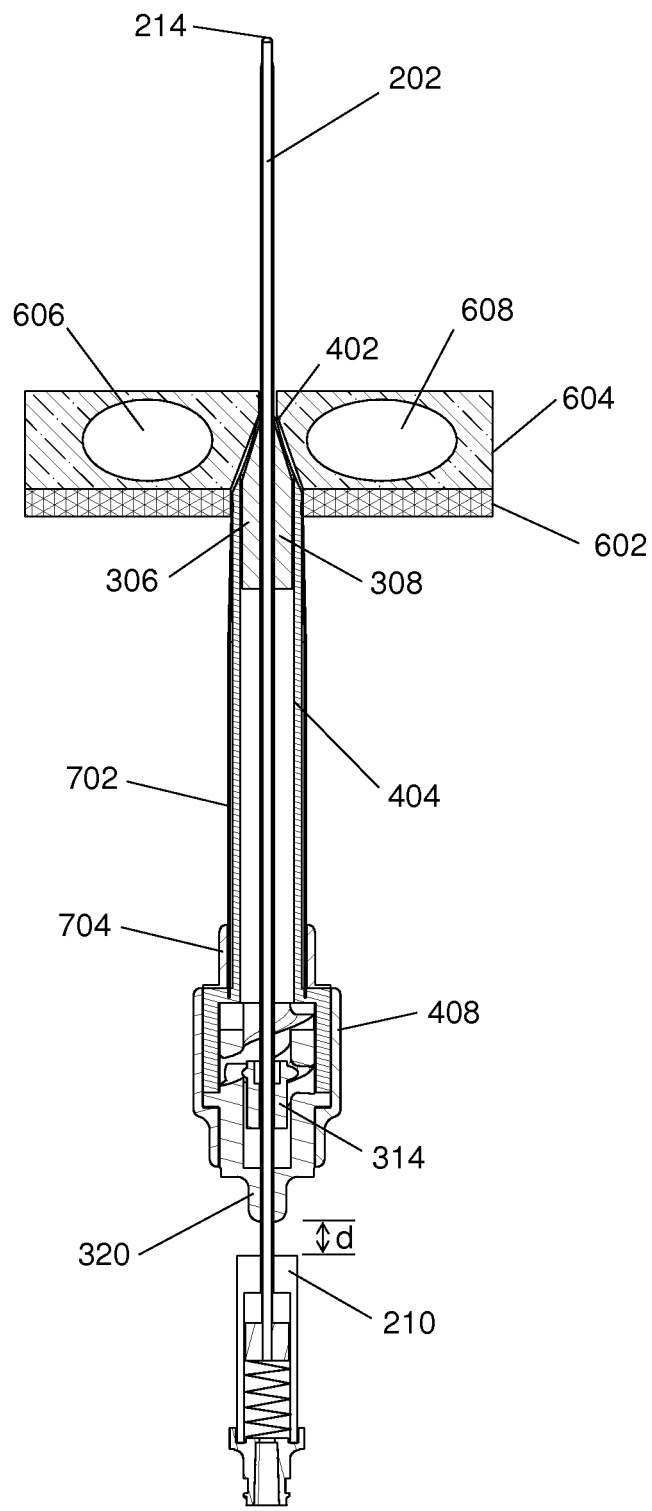
FIG. 7 illustrates a second step in inserting the insertion device according to aspects of the present invention.

Prior to inserting device 100 into a patient, a user will palpate the skin to determine the appropriate insertion point between ribs 606 and 608. Once the desired location is found, the user begins to insert insertion device 100. While not shown in FIG. 6, when first inserting insertion device into the patient, blades 306 and 308 are not deployed and are located within obturator assembly 106 (similar to the device as shown in FIG. 7).

When inserting insertion device 100 into the patient, safety needle 102 is the first component to contact the patient's skin 602. As described with reference to FIG. 2, pushing safety needle 102 against the patient's skin 602 causes stylet 206 to retract, exposing the sharp cannula tip 204 to the skin. As the user continues to push, cannula tip 204 cuts through skin 602 and soft tissue 604. Soft tissue 604 may include muscle, fat, fascia, or any other soft tissues with which safety needle 102 may come in contact with during the procedure.

A skilled user can generally tell when the desired location is reached, as a distinct decrease in resistance occurs. The decrease in resistance is an indication that safety needle 102 has reached the desired, fluid-filled location. To confirm that safety needle 102 has reached the desired location, the user will attach a fluid drainage device to hub 212 via connection means 216. The user will then attempt to drain fluid from the area. If the desired fluid is drawn from the area, the user may continue with the procedure. If the desired fluid is not drawn from the area, the user may need to continue in attempts to find the desired location.

Assuming the desired fluid has been located, the user then deploys blades 306 and 308 by turning handle 320 until handle 320 cannot be turned any more, meaning blades 306 and 308 are fully deployed. The user then advances insertion device 100 until blades 306 and 308 enter skin 602 to create a skin nick. If desirable, after creating the skin nick, the user may pull insertion device back such that blades 306 and 308 are not in skin 602, rotate insertion device 100 90 degrees, and then advance insertion device again until blades 306 and 308 enter skin 602. After one or more skin nicks are created, the user turns handle 320 in the opposite direction until it cannot be turned any more, meaning blades 306 and 308 are fully retracted. The user can then further advance insertion device 100, which is further described with reference to FIG. 7.

In an alternate method, the user may deploy blades 306 and 308 first, create a skin nick, and then retract blades 306 and 308. The user may then proceed with inserting safety needle 102 into the patient as previously described, or the user may decide to forego using safety needle 102 and instead insert obturator assembly 106, blade assembly 104, and dilator assembly 108 into the desired space within the patient.

FIG. 7 illustrates a second step in inserting the insertion device according to aspects of the present invention.

As shown in the figure, insertion device 100 is pushed further into the patient. As insertion device 100 advances, obturator tip 402 expands the pathway created by safety needle 102 and the one or more skin nicks. The user holds safety needle 102 with one hand while advancing obturator assembly 106, blade assembly 104, and dilator assembly 108. The distance between housing 210 and handle 320, noted as "d", will increase as the user continues to advance obturator assembly 106, blade assembly 104, and dilator assembly 108.

When obturator tip 402 reaches stylet tip 214, the user may stop advancement. The user may use an appropriate imaging technique to determine when obturator tip 402 reaches stylet tip 214. In an alternate embodiment, cannula 202 may include an indicator mark, such that when handle 320 no longer covers the indicator mark, obturator tip 402 has reached stylet tip 214.

The user can then remove components to prepare the patient for insertion of a catheter. Safety needle assembly 102, blade assembly 104, and obturator assembly 106 may all be removed from dilator assembly 108 at the same time. To remove the components, the user will grip dilator shaft 702 with one hand and handle cover 408 with the other hand. Dilator shaft 702 will be further described with reference to FIG. 8. While holding dilator shaft 702 steady, the user will pull back on handle cover 408. This will serve to detach Safety needle assembly 102, blade assembly 104, and obturator assembly 106 from the press-fit connection to dilator assembly 108. As the user continues to pull back on handle cover 408, all components will be removed from dilator assembly 108, leaving dilator assembly 108 in the body.

Figure 8:
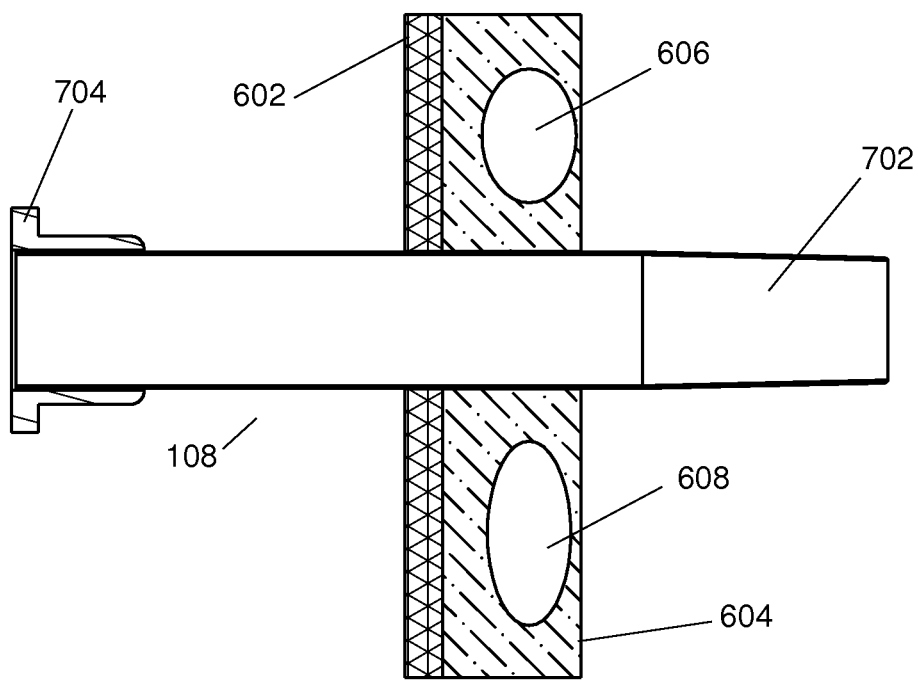
FIG. 8 illustrates a final step in inserting the insertion device according to aspects of the present invention.

FIG. 8 illustrates a final step in inserting the insertion device according to aspects of the present invention.

As shown in the figure, dilator assembly 108 is in the patient. Dilator assembly 108 includes dilator shaft 702 and dilator hub 704. Dilator shaft 702 is preferably made of plastic and may be extruded, molded, or manufactured in any other known way to create the desired geometry. Dilator hub 704 is also preferably made of plastic by any known method to create the desired geometry. Dilator hub 704 and dilator shaft 702 are connected by any known methods that would serve to prevent any relative motion between the two components.

At this point in the procedure, the user will typically place a catheter through the lumen of dilator shaft 702 to reach the desired location within the body. Essentially, dilator shaft 702 is simply a conduit through which another device (i.e., a catheter) is placed. Once the catheter is placed in the desired location, dilator assembly 108 is removed from the patient. The user then completes the procedure by closing skin 602 around the catheter.

Figure 9:
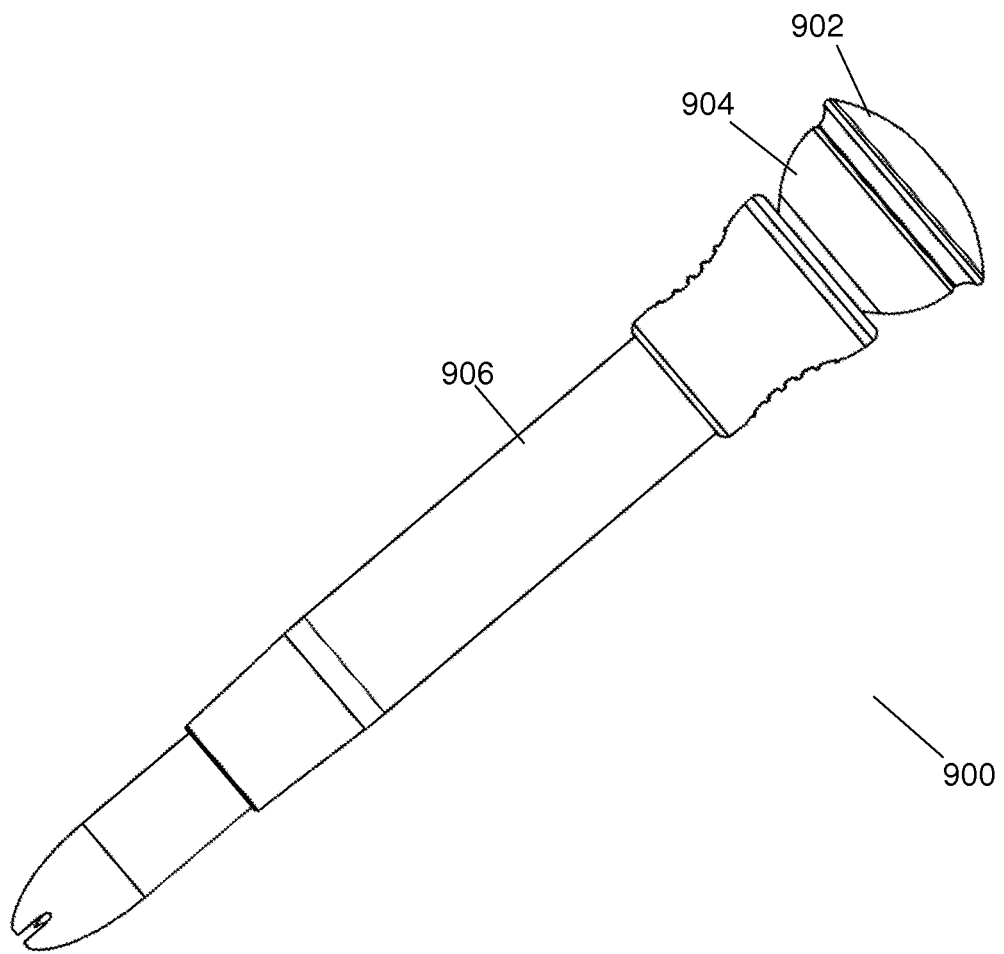
FIG. 9 illustrates an alternate embodiment of an insertion device according to aspects of the present invention.

FIG. 9 illustrates an alternate embodiment of an insertion device according to aspects of the present invention.

As shown in the figure, insertion device 900 includes stylet assembly 902, obturator assembly 904, and dilator assembly 906. Obturator assembly 904 also includes a blade assembly that will be further described with reference to FIGS. 11-12. Specific aspects of stylet assembly 902, obturator assembly 904, and dilator assembly 906 will be further described with reference to FIGS. 10-12.

Figure 10:
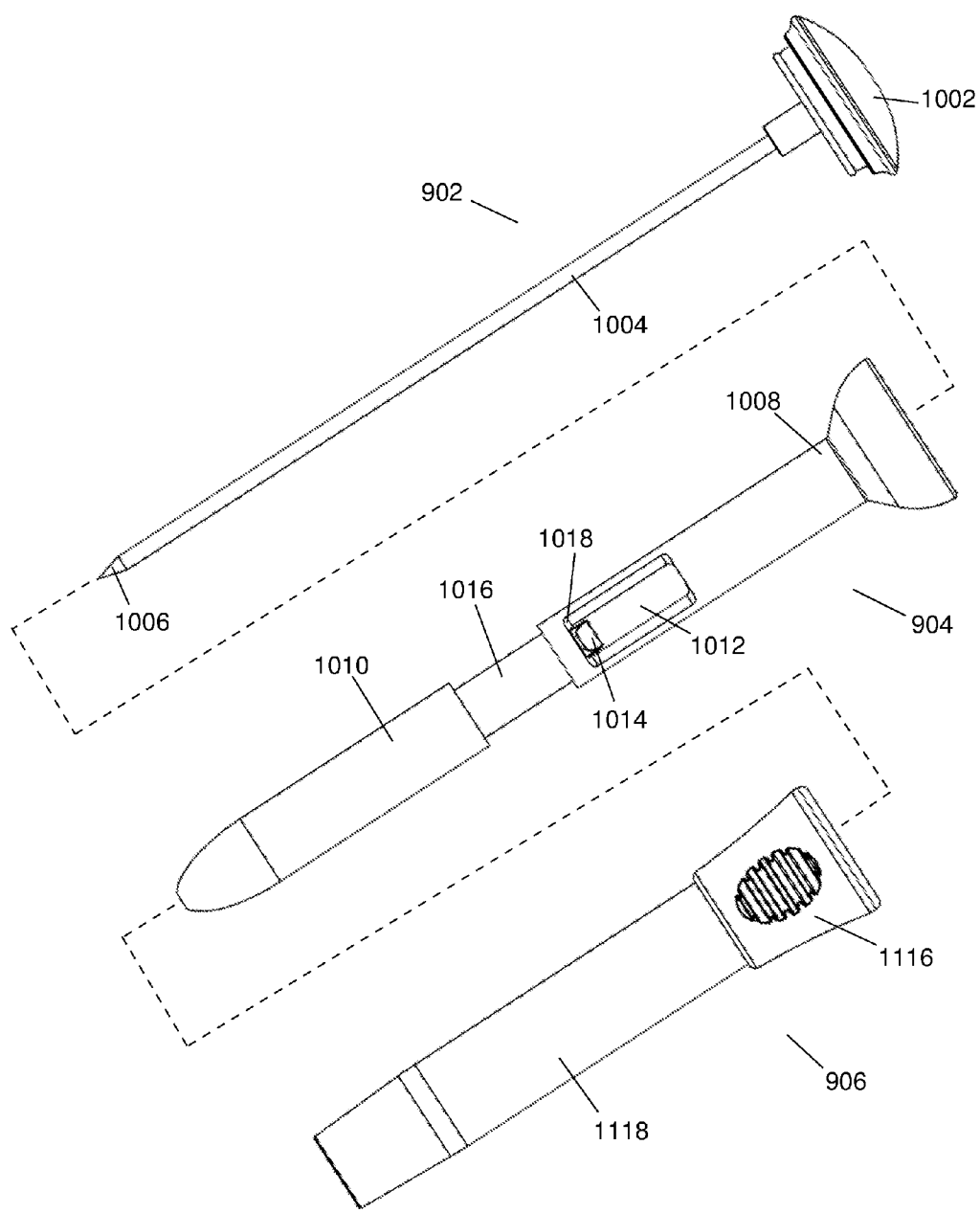
FIG. 10 illustrates the process by which an alternate embodiment of the insertion device is assembled.

FIG. 10 illustrates the process by which an alternate embodiment of the insertion device is assembled.

As shown in the figure, stylet assembly 902 includes handle 1002, shaft 1004, and tip 1006.

Handle 1002 is a rigid body and is preferably made of plastic, however any other rigid material would suffice.

Handle 1002 is operable to connect to shaft 1004 and provide a gripping surface for the user.

Shaft 1004 is a rigid body and is preferably made of metal, more preferably made of stainless steel. Shaft 1004 is operable to connect to handle 1002. The connection between shaft 1004 and handle 1002 should be strong enough to prevent the parts from separating and to prevent relative motion between the two components.

Tip 1006 is the distal end of shaft 1004. Preferably, tip 1006 is sharp enough to cut through tissue, and the sharpness may be created using any known method, such as grinding or EDM. Preferably, tip 1006 is not a separate component from shaft 1004, but the end of shaft 1004 is machined to create tip 1006. In some embodiments, though, tip 1006 may be a separate component from shaft 1004, and the two components may be connected by any process which would create a strong bond between the two components.

The individual components of stylet assembly 902 may all be manufactured separately and then connected together, but in alternate embodiments stylet assembly 902 may be a single, continuous component.

Obturator assembly 904 includes obturator top 1008, obturator bottom 1010, window 1012, tab 1014, obturator middle 1016, and ledge 1018. Preferably, obturator assembly 904 includes two windows and two tabs to maintain symmetry, however for purposes of brevity only one window and one tab is shown. All components of obturator assembly 904 are preferably made from plastic, however any other material that can be used to accomplish the objectives of obturator assembly 904 may be used. Obturator assembly also includes a blade assembly (not shown) that will be further described with reference to FIGS. 11-12.

Obturator top 1008 and obturator bottom 1010 are manufactured with the same outer diameter. Obturator middle 1016 is rigidly connected to obturator bottom 1010 and has an outer diameter that is smaller than the inner diameter of obturator top 1008, such that obturator middle can slidably fit within obturator top 1008.

Tab 1014 is rigidly connected to the outer diameter of obturator middle 1016, and is operable to slide within window 1012 and rest on ledge 1018.

Obturator bottom 1010, obturator middle 1016, and tab 1014 are described above as separate components, however they are preferable a single component in order to avoid additional connections.

In operation, obturator assembly 904 is assembled by inserting obturator middle 1016 into obturator top 1008 until tab 1014 passes ledge 1018 and fits within window 1012. To accomplish this, obturator middle may need to have a discontinuous diameter, such that tab 1014 can be slightly deflected to allow tab 1014 to enter obturator top 1008. To create a discontinuous diameter, a slot may be introduced into obturator middle 1016, thus creating two halves of obturator middle 1016. As obturator middle 1016 slides into obturator top 1008, the two halves of obturator middle 1016 would deflect toward one another, allowing tab 1014 to fit within the inner diameter of obturator top 1008. Once tab 1014 passes ledge 1018 and reaches window 1012, tab 1014 will pop into window 1012 and the two halves of obturator middle 1016 will no longer be deflected toward each other.

Thus, obturator assembly 904 is created, where obturator middle 1016 can slide within obturator top 1008, causing obturator bottom 1010 to advance and retract.

Dilator assembly 906 includes grip 1116 and dilator shaft 1118. Both grip 1116 and dilator shaft 1118 are preferably made from plastic, but any rigid material would suffice. grip 1116 and dilator shaft 1118 are rigidly connected such that there is no relative motion between the two components. In an alternate embodiment, grip 1116 and dilator shaft 1118 may be a single component.

In operation, and to assembly access device 900, stylet assembly is inserted through the lumen (not shown) of obturator assembly 904. Handle 1002 of stylet assembly 902 may rest on obturator top 1008 such that handle 1002 may easily slide in and out without any resistance. In an alternate embodiment, handle 1002 may releasably connect with obturator top 1008 such that handle 1002 must be disconnected from obturator top 1008 before sliding stylet assembly 902 out of obturator assembly 904. As a non-limiting example, the connection between handle 1002 and obturator top 1008 may be a press fit connection.

Next, the combination of stylet assembly 902 and obturator assembly 904 is inserted through the lumen (not shown) of dilator assembly 906. Obturator top 1008 may rest on grip 1116 such that obturator 904 may easily slide in and out without any resistance. In an alternate embodiment, obturator top 1008 may releasably connect with grip 1116 such that obturator top 1008 must be disconnected from grip 1116 before sliding obturator assembly 904 out of dilator assembly 906. As a non-limiting example, the connection between obturator top 1008 and grip 1116 may be a press fit connection.

Figure 11:
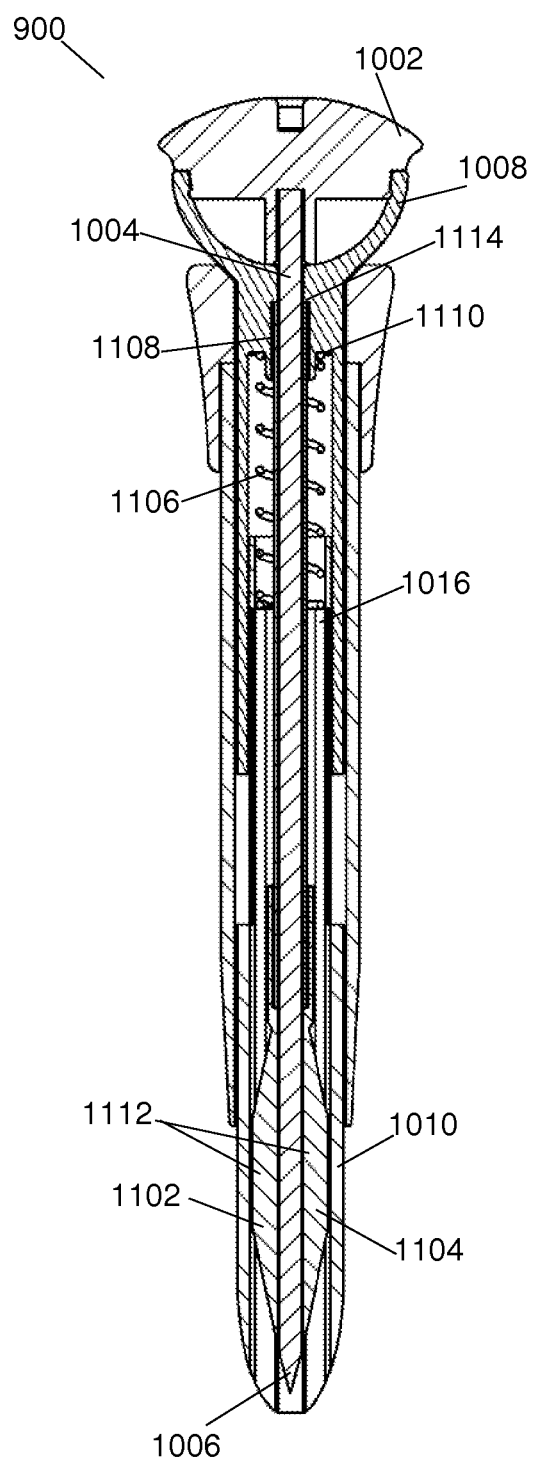
FIG. 11 illustrates a cross section of an alternate embodiment of the insertion device in a first configuration.

FIG. 11 illustrates a cross section of an alternate embodiment of the insertion device in a first configuration.

As shown in the figure, device 900 includes blades 1102 and 1104, spring 1106, blade tube 1108, and wall 1110. The combination of blades 1120 and 1104, and blade tube 1108 makes up blade assembly 1112.

Blade tube 1108 is connected to blades 1102 and 1104. The connection is preferably a welded connection, however other connection means may be employed. As a non-limiting example, blade tube 1108 may contain one or more slots at its distal end and blades 1102 and 1104 may contain one or more matching slots such that blades 1102 and 1104 may be assembled on to blade tube 1108 by sliding slotted sections of blades 1102 and 1104 on to the corresponding slots at the distal end of blade tube 1108.

Blades 1102 and 1104 are preferably constructed from metal, more preferably from stainless steel, however any material suitable for medical applications would suffice. Blades 1102 and 1104 are operable to cut the skin of a patient, and as such are sufficiently sharp to cut skin. The specific shape, grind angles, and tip angles may be of any dimensions such that the effect of cutting skin may be accomplished. Blades 1102 and 1104 are attached to blade tube 1108 as previously described.

Spring 1106 contacts obturator middle 1016 and wall 1110 of obturator top 1008. Spring 1106 is operable to bias obturator middle 1016 away from obturator top 1008.

Assembling blade assembly 1112 to obturator assembly 904 begins when obturator top 1008 is not connected to obturator middle 1016. First, spring 1106 is inserted into obturator top 1008 until it contacts wall 1110. Spring 1106 may be bonded to wall 1110, however bonding is not required. Next, blade assembly 1112 is bonded to obturator top 1008 by inserting blade tube 1108 through spring 1106 until it contacts wall 1114. Preferably, blade assembly 1112 is bonded to obturator top 1008 by using adhesive between blade tube 1108 and wall 1114, however any other bonding method that rigidly secures blade assembly 1112 to obturator top 100 is sufficient. Third, obturator middle 1016 and obturator bottom 1010, slide over blade assembly 1112 until the tabs of obturator middle 1016 lock into the windows of obturator top 1008 as described with reference to FIG. 10. This method of assembly will require slots along obturator middle 1016 and obturator bottom 1010 to accommodate blades 1102 and 1104. The slots will allow obturator middle 1016 to flex, as described with reference to FIG. 10, when inserting obturator middle 1016 into obturator top 1008. With obturator middle 1016 attached to obturator top, spring 1106 is in contact with obturator middle 1016 and wall 1110. The slots described that accommodate blades 1102 and 1104 go through the outer diameter of obturator middle 1016, but not through the outer diameter of obturator bottom 1010 because the outer diameter of obturator bottom 1010 is larger than the width of blades 1102 and 1104 and the diameter of blade tube 1108 combined.

Obturator assembly 904 now includes blade assembly 1112, and device 900 can be assembled together as described with reference to FIG. 10.

In this configuration, obturator bottom 1010 covers both tip 1006 and blades 1102 and 1104 because spring 1106 biases obturator bottom 1010 away from obturator top 1008. To bias obturator bottom 1010 toward obturator top 1008 would require a force pushing obturator bottom 1010 toward obturator top 1008 that is larger than the force of spring 1106 that pushes the two components apart.

Figure 12:
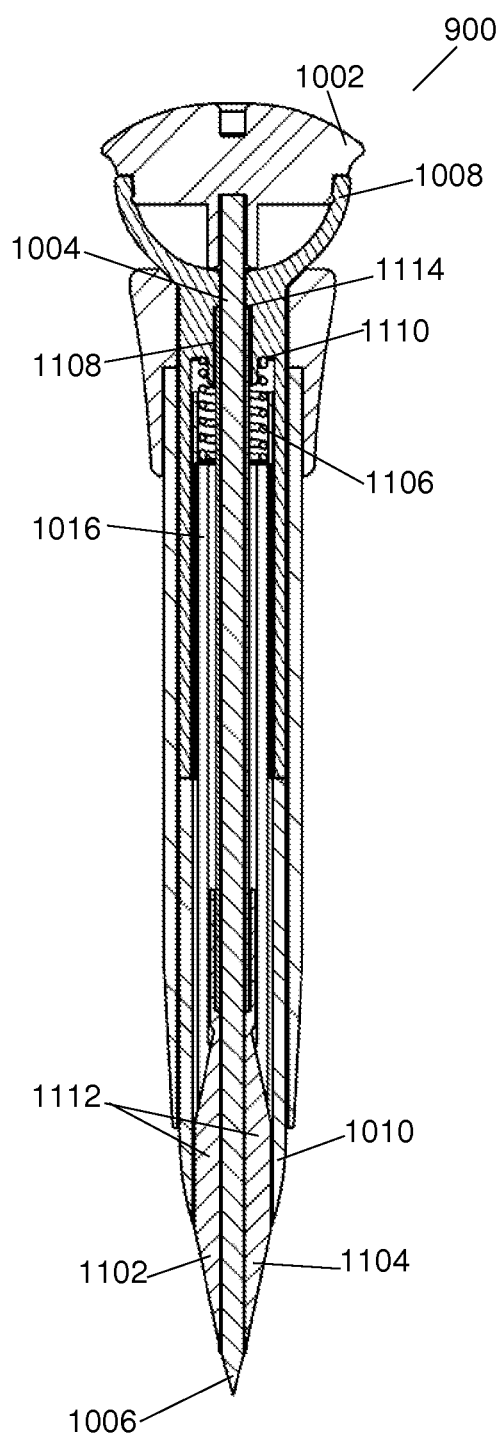
FIG. 12 illustrates a cross section of an alternate embodiment of the insertion device in a second configuration.

FIG. 12 illustrates a cross section of an alternate embodiment of the insertion device in a second configuration.

In this configuration, a force has pushed obturator bottom 1010 toward obturator top 1008, causing spring 1106 to compress as obturator bottom 1010 moves toward obturator top 1008. As obturator bottom 1010 moves toward obturator top 1008, tip 1006 and blades 1102 and 1104 are exposed and can be used for cutting tissue.

In operation, and with reference to FIGS. 11 and 12, a user would determine the correct insertion point on the patient using any typical method, and proceed to place device 900 at the desired insertion point on the patient's skin. Tip 1006 and blades 1102 and 1104 are covered by obturator bottom 1010 at this point, shielding the patient (and the user) from a careless needle stick. To begin inserting device 900, the user pushes down on handle 1002, which pushes obturator bottom 1010 onto the patient's skin. As the user increases the force applied to handle 1002, obturator bottom 1010 begins to move toward obturator top 1008, causing obturator middle 1016 to begin compressing spring 1106. As the user continues to increase the force applied to handle 1002, obturator bottom 1010 will move enough to begin to expose tip 1006 and blades 1102 and 1104. As tip 1006 and blades 1102 and 1104 are exposed, they puncture the patient's skin and device 900 begins to move into the patient. The deeper the user pushes device 900 into the patient, the more obturator bottom 1010 is retracted to expose tip 1006 and blades 1102 and 1104 until obturator bottom 1010 is fully retracted.

When the user reaches the desired area, which is typically filled with fluid, a noticeable decrease in pushing force is required. When the user feels the decreased force, he will typically stop pushing the device further into the patient. As an extra level of protection for the patient, though, when the force required to push device 900 through tissue is reduced or eliminated once the desired location is reached, spring 1106 will force obturator bottom 1010 away from obturator top 1008, and obturator bottom will cover tip 1006 and blades 1102 and 1104 to protect the patient.

At this point, the user may want to confirm that device 900 is in the correct location. To obtain confirmation, the user would remove stylet assembly 902 from obturator assembly 904, leaving an open lumen through obturator assembly 904 into the patient. Device 900 may also include a safety needle like safety needle assembly 102. The user could insert the safety needle through the open lumen of obturator assembly 904 into the desired location and proceed to aspirate fluid to confirm that device 900 is in the correct location. The safety needle would still provide additional safety for the patient because it would prevent the user from pushing the safety needle too far beyond the desired location when attempting to aspirate fluid.

After the user confirms that device 900 is in the desired location, the user can remove the safety needle and obturator assembly 904 from dilator assembly 906, The user would then insert a catheter through the lumen of dilator assembly 906, remove dilator assembly 906 from the patient, and complete the procedure by closing the skin around the catheter.

In an alternate embodiment, the user may choose to use a safety needle instead of stylet assembly 902 when inserting the device to the desired location. In that case, the user would replace stylet assembly 902 with a safety needle through the lumen of obturator assembly 904, then insert safety needle to the desired location and aspirate fluid to confirm placement. After placement is confirmed, the user may choose to advance obturator assembly 904 in a manner similar to that described above. When obturator 904 reaches the desired location already occupied by the tip of the safety needle, obturator bottom 1010 would be propelled forward by spring 1106 to protect the patient from further injury. The safety needle and obturator assembly 904 would be removed from dilator assembly 906 so the user could continue the procedure.

In yet another alternate embodiment, once the location is confirmed by aspirating fluid using the safety needle, the user may choose to remove the safety needle and replace it with stylet assembly 902. The user would advance device 900 as described above, however the user would know before the insertion that the desired location is the correct location because of the previous confirmation with the safety needle. The procedure would then continue as described above with reference to FIGS. 11-12.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A device to access interior body regions comprising:
a safety needle assembly operable to create a pathway through skin and into said interior body regions, said safety needle assembly further comprising a hub connected to a housing, a spring disposed within an open center of the housing, a cannula connected to said housing at a proximal end of said cannula, a stylet connected to said spring at a proximal end of said stylet, said stylet extending through an inner diameter of said cannula, said stylet further including a blunt stylet tip at a distal end of said stylet, wherein said blunt stylet tip is closed at said distal end of said stylet, and wherein said cannula includes a sharp cannula tip at a distal end of said cannula;
a stylet assembly operable to expand the pathway through skin and into said interior body regions, said stylet assembly further comprising a handle connected to a shaft, said shaft further comprising a sharp tip at a distal end of said shaft;
a blade assembly operable to cut tissue to create a skin nick and provide access into said interior body regions, said blade assembly further comprising at least one blade connected to a blade tube at a distal end of said blade tube;
a retractable obturator assembly operable to expand said pathway into said interior body regions, said retractable obturator assembly further comprising an obturator bottom connected to an obturator middle, an obturator top sized and configured to allow said obturator middle to fit within an inner diameter of said obturator top, and an obturator spring sized and configured to fit between said obturator middle and a wall of said obturator top;
a dilator assembly operable to maintain said pathway and provide access to said interior body regions, wherein said dilator assembly is releasably attached to said obturator assembly;
wherein said obturator spring provides a biasing force that biases said obturator middle away from said obturator top; and
wherein said obturator assembly further comprises a tab on said obturator middle, said tab sized and configured to slidably fit within a window in said obturator top to prevent said obturator middle and said obturator top from separating under said biasing force.

2. The device of claim 1, wherein said safety needle assembly, said blade assembly, said retractable obturator assembly, and said dilator assembly can be used together to identify said interior body regions.

3. The device of claim 2, wherein said safety needle assembly can be removed from said blade assembly and replaced by said stylet assembly, and the combination of said stylet assembly, said blade assembly, said retractable obturator assembly, and said dilator assembly can be used together to access said interior body regions.

4. The device of claim 1, wherein said retractable obturator assembly retracts in response to a force imparted by body tissue, and advances upon removal of said force.

5. The device of claim 4, wherein said retractable obturator assembly prevents said blade assembly from contacting the skin of a patient or a user until said force imparted by body tissue is applied to said retractable obturator assembly.

6. A method of accessing interior body regions, comprising:
providing an access device defining:
a stylet assembly, a retractable obturator assembly; slidably connected to a blade assembly, and a dilator assembly, wherein said stylet assembly, said retractable obturator assembly, and said blade assembly are releasably attached to said dilator assembly;
combining said stylet assembly, said retractable obturator assembly, said blade assembly, and said dilator assembly together;
advancing said retractable obturator assembly against skin, wherein said advancing of said retractable obturator assembly against the skin imparts a force to said retractable obturator assembly, said force causing an obturator spring within said retractable obturator assembly to compress, said compression forcing an obturator bottom of said retractable obturator assembly to slide toward an obturator top of said retractable obturator assembly, exposing said stylet assembly and said blade assembly to contact the skin;

advancing said retractable obturator assembly through the skin and soft tissues into said interior body regions, wherein when said obturator bottom reaches said interior body regions, said force is removed, causing said obturator spring to expand, said expansion forcing said obturator bottom to slide away from said obturator top, covering said stylet assembly and said blade assembly and preventing said stylet assembly and said blade assembly from contacting said interior body regions; and disconnecting said stylet assembly, said retractable obturator assembly, and said blade assembly from said dilator assembly, leaving said dilator assembly in the skin and soft tissues to provide access to said interior body regions.

7. A method of accessing interior body regions, comprising:

providing an access device defining:

a safety needle assembly, a stylet assembly, a retractable obturator assembly; slidably connected to a blade assembly, and a dilator assembly, wherein said safety needle assembly, said stylet assembly, said retractable obturator assembly, and said blade assembly are releasably attached to said dilator assembly;

combining said safety needle assembly, said retractable obturator assembly, said blade assembly, and said dilator assembly together;

advancing said safety needle assembly through skin into said interior body regions;

confirming the position of said safety needle assembly by aspirating fluid through said safety needle assembly;

removing said safety needle assembly from said retractable obturator assembly;

inserting said stylet assembly through said retractable obturator assembly;

advancing said retractable obturator assembly against the skin, wherein said advancing of said retractable obturator assembly against the skin imparts a force to said retractable obturator assembly, said force causing an obturator spring within said retractable obturator assembly to compress, said compression forcing an obturator bottom of said retractable obturator assembly to slide toward an obturator top of said retractable obturator assembly, exposing said stylet assembly and said blade assembly to contact the skin;

advancing said retractable obturator assembly through the skin and soft tissues into said interior body regions, wherein when said obturator bottom reaches said interior body regions, said force is removed, causing said obturator spring to expand, said expansion forcing said obturator bottom to slide away from said obturator top, covering said stylet assembly and said blade assembly and preventing said stylet assembly and said blade assembly from contacting said interior body regions; and disconnecting said stylet assembly, said retractable obturator assembly, and said blade assembly from said dilator assembly, leaving said dilator assembly in the skin and soft tissues to provide access to said interior body regions.

\* \* \* \* \*